United States Patent
Lochtman et al.

(10) Patent No.: US 6,388,135 B1
(45) Date of Patent: May 14, 2002

(54) PREPARATION OF 4-BROMOANILINE DERIVATIVES

(75) Inventors: Rene Lochtman, Mannheim; Michael Keil, Freinsheim; Joachim Gebhardt, Wachenheim; Michael Rack, Heidelberg; Wolfgang von Deyn, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/894,006

(22) Filed: Jun. 29, 2001

Related U.S. Application Data

(60) Provisional application No. 60/219,410, filed on Jul. 20, 2000.

Foreign Application Priority Data

Jun. 30, 2000 (DE) .......................................... 100 30 975

(51) Int. Cl.[7] .............................................. C07C 209/00
(52) U.S. Cl. ........................ 564/412; 548/240; 548/247; 558/418
(58) Field of Search .......................... 564/412; 548/240, 548/247; 558/418

(56) References Cited

FOREIGN PATENT DOCUMENTS

| | | |
|---|---|---|
| CA | 2278331 | 7/1998 |
| WO | WO 98/31681 | 7/1998 |
| WO | WO 99/58509 | 11/1999 |

OTHER PUBLICATIONS

Müller et al. "Methoden Der Organischen Chemie" Band V/4 (1960) pp 240–242 & 274–249.

*Primary Examiner*—Samuel Barts
(74) *Attorney, Agent, or Firm*—Keil & Weinkauf

(57) ABSTRACT

A process for preparing 4-bromoaniline derivatives of the formula I

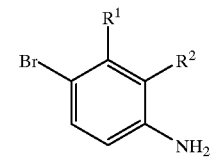

where:

$R^1$ is $C_1$–$C_6$-alkyl, $C_1$–$C_6$-haloalkyl, $C_1$–$C_6$-alkoxy, $C_1$–$C_6$-haloalkoxy, $C_3$–$C_8$-cycloalkyl, halogen $R^2$ is $C_1$–$C_6$-alkyl, $C_1$–$C_6$-alkoxy, $C_3$–$C_8$-cycloalkyl, $C_2$–$C_6$-alkenyl, cyano or a heterocyclic radical is described.

30 Claims, No Drawings

PREPARATION OF 4-BROMOANILINE DERIVATIVES

The present application claims priority of prior provisional application Serial No. 60/219,410, filed on Jul. 20, 2000.

The present invention provides a process for preparing 4-bromoaniline derivatives.

4-Bromoaniline derivatives are useful compounds which are used as intermediates in chemical industry. They are suitable, for example, for preparing active compounds used in the field of crop protection, or for preparing pharmaceutically active compounds. WO 99/58509, for example, describes processes for preparing isoxazolin-3-ylacylbenzenes in which 4-bromoaniline derivatives are employed as intermediates for preparing herbicidally active compounds. WO 98/31681 describes these active compounds (2-alkyl-3-(4,5-dihydroisoxazol-3-yl)acylbenzenes) as herbicidally active compounds.

It is known from the literature that the selective bromination of anilines in the para position is impossible, or possible only with difficulty (Houben-Weyl 5/4, 241, 274 ff). In general, bromination with elemental bromine is not selective, but frequently associated with the formation of considerable amounts of dibromo compounds. According to experience, the selectivities for monobromo to dibromo compounds are in an order of magnitude of about 9:1, i.e. the proportion of undesired dibromo compounds is about 10%. Thus, only with expensive reagents, such as tetrabutylammonium tribromide, the compound 4-bromo-2-(4,5-dihydroisoxazol-3-yl)-3-methylaniline, for example, was obtained at −30° C. in a yield of about 50% (cf. WO 99/58509).

It is an object of the present invention to provide an alternative process for preparing 4-bromoaniline derivatives. The preparation process described in WO 99/58509 for the 4-bromo-2-(4,5-dihydroisoxazol-3-yl)-3-methylaniline derivatives gives unsatisfactory yields and an unsatisfactory purity of the products. Accordingly, the process described in WO 99/58509 is only of limited use for the industrial preparation of such compounds.

We have found that this object is achieved by a process for preparing 4-bromoaniline derivatives of the formula I

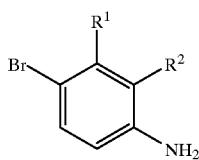

I where:

$R^1$ is $C_1$–$C_6$-alkyl, $C_1$–$C_6$-haloalkyl, $C_1$–$C_6$-alkoxy, $C_1$–$C_6$-haloalkoxy, $C_3$–$C_8$-cycloalkyl, halogen $R^2$ is $C_1$–$C_6$-alkyl, $C_1$–$C_6$-alkoxy, $C_3$–$C_8$-cycloalkyl, $C_2$–$C_6$-alkenyl, cyano or a heterocyclic radical, which comprises reacting a compound of the formula II

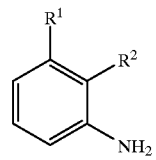

II in which $R^1$ and $R^2$ are as defined above with a brominating agent in the solvent pyridine or in a solvent mixture comprising at least 55% by wight of pyridine.

With the aid of the process according to the invention, it is possible to obtain the aniline derivatives of the formula I in higher yields than with the prior-art preparation processes. Thus, for example, the compound 4-bromo-2-(4,5-dihydroisoxazol-3-yl)-3-methylaniline can be obtained by the process described in WO 99/58509 (cf. Example 10 therein) in a yield of only 47%, whereas the yield in the process according to the invention is at least 60%, preferably at least 70% or 80%, and in particular at least 90%.

Moreover, the compounds of the formula I are obtained in higher purity. Here, the bromination takes place with high selectivity in the 4-position of the phenyl ring. The selectivity (ratio of monobromo to dibromo compound) is at least 92:8, in particular at least 95:5. Surprisingly, the proportion of impurities, such as, for example, dibromides (these dibromides are derivatives of the formula I which are substituted in the 5- or 6-position by a further bromine atom) which are difficult to remove from the resulting reaction mixture, or whose removal requires relatively high technical expenditure, is less than 5%. Accordingly, the number of further additional purification steps for isolation and work-up of the compounds I prepared by the process according to the invention can be reduced. This is particularly advantageous for the industrial production of the compounds I, since a more efficient and more cost-effective process can be provided.

Owing to the high selectivity and the small proportion of dibromo compounds, it is possible, if appropriate, to use the reaction product even without additional purification for the next process steps for further conversion into suitable end products.

$C_1$–$C_6$-Alkyl is a straight-chain or branched alkyl group having 1–6 carbon atoms, such as, for example, methyl, ethyl, n-propyl, isopropyl, n-butyl, isobutyl, tert.-butyl, n-pentyl or n-hexyl; preference is given to $C_1$–$C_4$-alkyl, such as, for example, methyl, ethyl, n-propyl, isopropyl, n-butyl, isobutyl or tert.-butyl.

$C_1$–$C_6$-haloalkyl is a straight-chain or branched $C_1$–$C_6$-alkyl group as mentioned above which is partially or fully substituted by fluorine, chlorine, bromine and/or iodine, for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromoethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl; perference is given to $C_1$–$C_4$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2,-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, or nonafluorobutyl;

$C_1$–$C_6$-Alkoxy is a straight-chain or branched alkyl group having 1–6 carbon atoms, such as, for example, methoxy, ethoxy, n-propyloxy, isopropyloxy, n-butyloxy, isobutyloxy, tert.-butyloxy, n-pentyloxy or n-hexyloxy; preference is given to $C_1$–$C_4$-alkoxy, such as, for example, methoxy, ethoxy, n-propyloxy, isopropyloxy, n-butyloxy, isobutyloxy or tert.-butyloxy;

$C_1$–$C_6$-haloalkoxy is a straight-chain or branched $C_1$–$C_6$-alkoxy group as mentioned above which is partially or fully substituted by fluorine, chlorine, bromine and/or iodine, for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2, difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy; perference is given to $C_1$–$C_4$-haloalkoxy, such as fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2,difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, or nonafluorobutoxy;

$C_3$–$C_8$-Cycloalkyl is an unsubstituted or substituted cycloalkyl ring having 3–8 carbon atoms, such as, for example, cyclopropyl, cyclobutyl, cyclopentyl, cyclohexyl, cycloheptyl or cyclooctyl, Suitable substituents are, for example: $C_1$–$C_6$-alkyl, $C_1$–$C_6$-alkoxy or halogen; preference is given to $C_3$–$C_6$-cycloalkyl, which is unsubstituted, such as, for example cyclopropyl, cyclopentyl or cyclohexyl;

$C_2$–$C_6$-alkenyl is a straight-chain or branched alkenyl group having 2–6 carbon atoms, wherein the double bond is located at the connecting position, such as for example ethenyl, prop-1-en-1-yl, 1-methylethenyl, buten-1-yl, 1-methylprop-1-en-1-yl, 2-methylprop-1-en-1-yl, penten-1-yl, 1-methyl-but-1-en-1-yl, 2-methyl-but-1-en-1-yl, 3-methyl-but-1-en-1-yl, 1,2-dimethyl-prop-1-en-1-yl, hex-1-en-1-yl, 1-methylpent-1-en-1-yl, 2-methylpent-1-en-1-yl, 3-methylpent-1-en-1-yl, 4-methylpent-1-en-1-yl, 1,2-dimethylbut-1-en-1-yl, 1,3-dimethylbut-1-en-1-yl, 2,3-dimethylbut-1-en-1-yl, 3,3-dimethylbut-1-en-1-yl, 1-ethylbut-1-en-1-yl, 2-ethylbut-1-en-1-yl or 1-ethyl-2-methylprop-1-en-1-yl;

Halogen is fluorine, chlorine, bromine, is particular chlorine or bromine.

"Heterocyclic ring" is a saturated, unsaturated or partially unsaturated heterocycle having 3–8 ring atoms and one, two or three oxygen, sulfur or nitrogen atoms. Preference is given to heterocycles which contain at least one oxygen and/or one nitrogen atom. Preference is furthermore given to heterocycles having 5 or 6 ring atoms. The heterocycle can be attached to the phenyl ring at any site of the heterocycle, for example via a heterocyclic nitrogen ring atom or a carbon ring atom. The heterocycles are unsubstituted or mono-, di- or trisubstituted. Suitable substituents are radicals which are chemically inert under the chosen reaction conditions, such as, for example, $C_1$–$C_6$-alkyl, $C_1$–$C_6$-alkoxy or halogen. Suitable heterocyclic rings in the context of the present invention are, for example, the following heterocycles: pyrrolyl, pyrazolyl, imidazolyl, oxazolyl, isoxazolyl, thiazolyl, thiadiazolyl, piperidinyl, morpholinyl, oxazinyl, isoxazolinyl, isoxazolidinyl, etc. Preference is given to the following heterocycles: isoxazolyl, isoxazolinyl or isoxazolidinyl, in particular 4,5-dihydroisoxazol-3-yl or 4,5-dihydroisoxazol-5-yl.

The process according to the invention is preferably suitable for preparing compounds of the formula I, wherein the meaning of the substituents is as follows:

$R^1$ $C_1$–$C_6$-alkyl, $C_1$–$C_6$-alkoxy, $C_3$–$C_8$-cycloalkyl, halogen $R^2$ $C_1$–$C_6$-alkyl, $C_1$–$C_6$-alkoxy, $C_3$–$C_8$-cyloalkyl, cyano or a heterocyclic radical.

The process according to the invention is preferably suitable for preparing the following compounds of the formula I:

4-bromo-2-(4,5-dihydroisoxazol-3-yl)-3-methylaniline,
4-bromo-2-(4,5-dihydroisoxazol-3-yl)-3-ethylaniline,
4-bromo-2-(4,5-dihydroisoxazol-3-yl)-3-methoxyaniline,
4-bromo-2-(4,5-dihydroisoxazol-3-yl)-3-ethoxyaniline,
4-bromo-2-(3-methyl-4,5-dihydroisoxazol-5-yl)-3-methylaniline,
4-bromo-2-(3-methyl-4,5-dihydroisoxazol-5-yl)-3-ethylaniline,
4-bromo-2-(3-methyl-4,5-dihydroisoxazol-5-yl)3-methoxyaniline,
4-bromo-2-(3-methyl-4,5-dihydroisoxazol-5-yl)-3-ethoxyaniline,
4-bromo-2-(isoxazol-3-yl)-3-methylaniline,
4-bromo-2-(isoxazol-3-yl)-3-ethylaniline, 4-bromo-2-(isoxazol-3-yl)-3-methoxyaniline,
4-bromo-2-(isoxazol-3-yl)-3-ethoxyaniline,
4-bromo-2-(5-methylisoxazol-3-yl)-3-methylaniline,
4-bromo-2-(5-methylisoxazol-3-yl)-3-ethylaniline,
4-bromo-2-(5-methylisoxazol-3-yl)-3-methoxyaniline,
4-bromo-2-(5-methylisoxazol-3-yl)-3-ethoxyaniline,
4-bromo-2-cyano-3-methylaniline,
4-brom-2-cyano-3-methoxyaniline.

The reaction of the compounds II with a brominating agent is preferably carried out by the following process steps:

According to the invention, the reaction is carried out in the solvent pyridine, or in solvent mixtures comprising at least 55% by weight, preferably 80% by weight of pyridine. In the case of solvent mixtures, suitable additional solvents in the mixture with pyridine are, for example, alcohols such as methanol, or ethanol, preferably methanol; esters such as alkyl acetate or butyl acetate, preferably ethyl acetate or butyl acetate; amides, such as for example, N,N-dimethylformamide or N,N-dimethylacetamide; or water.

Initially, the compound II is charged in pyridine or a pyridine-containing solvent mixture, as solution or suspension. The brominating agent is then added over a period of 5 minutes–5 hours. The brominating agent is added either directly, i.e. without solvent, or together with a suitable solvent.

Preferred brominating agents are elemental bromine or a mixture of HBr and hydrogen peroxide. In the case of bromine, the bromine is preferably added together with a suitable solvent, such as, for example, pyridine, with formation of pyridinium perbromide. In this case, a particularly high selectivity in the ratio of monobromo to dibromo compound is achieved.

In a preferred embodiment of the process, the brominating agent and the compound II are employed in a molar ratio of from 1:1 to 2:1. The brominating agent is preferably employed in equimolar amounts, or in a slight excess.

The reaction is carried out at temperatures of from 20° C. to the boiling point of the solvent, preferably in the range from 60° C. to 85° C. In a further preferred embodiment, the reaction is carried out at temperatures of from 50° C. to 120° C., preferably in a range from 80° C. to 100° C., and especially at about 100° C.

The reaction time is 1–24 hours; preferably 2–12 hours, in particular 5–8 hours. In a further preferred embodiment the reaction time is 30 minutes to 10 hours, preferably 30 minutes to 5 hours.

If the brominating agent used is a mixture of HBr and hydrogen peroxide, the brominating agent is added to the solution of II over a period of preferably from 10 minutes to 3 hours. The molar ratio of HBr to compound II is preferably in the range of from 1:1 to 1.5:1. The addition is carried out at temperatures of 0–50° C., preferably 20–40° C. The hydrogen peroxide is then added. The molar ratio of $H_2O_2$ to HBr is from 1:1 to 1.5:1. The addition is carried out at temperatures of from 10° C. to the boiling point of the solvent, preferably from 50° to 120° C., especially from 80° C. to 100° C., especially preferably at about 100° C.; in a further preferred embodiment the addition is carried out preferably from 60° C. to 85° C. The solution is then stirred for a period of 10 min–36 hours, preferably 10 min–8 hours. In a further embodiment the solution is further stirred for a period of 1 to 36 hours, preferably 2 to 8 hours. In a further embodiment the solution is further stirred for a period of 10 min to 3 hours, preferably 10 min to 2 hours. Subsequently, the product is worked up and purified. To this end, the solution is concentrated and the crude product is dissolved in a suitable solvent, preferably pyridine or a solvent mixture comprising at least 50% pyridine, and admixed with water. Filtration and washing of the residue or crystallization using a suitable solvent (for example water) gives the product in good yield and high purity.

It is also possible to take up the crude product in dimethyl disulfide and to wash it with water or sodium hydroxide solution. The organic solution may be used directly in a further reaction.

In a preferred embodiment the compound of the formula II and pyridine or a mixture of puridine and water are initially taken. In the latter case, the ratio of pyridine to water is in the range of 80% to 98% by weight: 20% to 5% by weight, preferably in the range of 90 to 95% by weight: 10 to 5% by weight.

The ratio of the compound of the formula II to pyridine or pyridine/water is selected in such a way that a 5 to 25% by weight, preferably 10 to 15% by weight solution results. Then 0.8 to 1.1 mol-equivalents, preferably 0.9 to 1.0 mol-equivalents of HBr are added to the resulting solution. After removal of the water by azeotropic distillation, hydrogen peroxide is added to the remaining solution within 1 to 3 hours, preferably 1.5 to 2.5 hours at 50 to 120° C. preferably 80 to 110° C., and especially at about 100° C. Usually the hydrogen peroxide is a 20% to 50% by weight, preferably a 30% to 50% by weight preferably a 30% to 50% by weight aqueous solution. Subsequently the solution is stirred for a period of 10 minutes to 2 hours, preferably 30 minutes to 1 hour.

Subsequently, the product is worked up. To this end the reaction solution is cooled to about room temperature, and if necessary washed with aqueous sodium sulfite solution. The crude product obtained can be used for the next reaction step without further purification. It is also possible to take up the residue in dimethyl disulfide, to wash the resulting solution with water or sodium hydroxide solution and to use the resulting organic phase in the next reaction step.

In a further embodiment it is possible to mix pyridine, which may contain up to 10% water, with HBr und to remove the water by azeotropic distillation. Then the compound of the formula II is dissolved in the reaction mixture and hydrogen peroxide added. Both the ratios of the compounds need and the time and temperature profiles are as above.

In a further embodiment it is also possible to use pyridinium hydrobromide instead of pyridine and HBr.

If the brominating agent used is elemental bromine, the brominating agent is preferably added to the solution of II a little at a time or contionuously over a period of from about 30 minutes to 6 hours. The molar ratio of bromine to the compound II is preferably in the range from 1:1 to 1.5:1. The addition is carried out at temperatures of 0–50° C., preferably at room temperature. The solution is then stirred for a period of 1–24 hours, preferably 2–8 hours. Subsequently, the product is worked up and purified. To this end, the solution is concentrated and the crude product is dissolved in a suitable solvent, preferably pyridine or a solvent mixture comprising at least 50% pyridine, and admixed with water. Filtration and washing of the residue or crystallization using a suitable solvent (for example water) gives the product is good yield and high purity.

Furthermore, the product can also be obtained from the reaction solution by extraction. To this end, the reaction solution is initially concentrated and the residue is taken up in a suitable solvent or solvent mixture, the components being selected, for example, from water, ethyl acetate and dimethyl disulfide (DMDS), in particular water, ethyl acetate, water/ethyl acetate or water/DMDS. Suitable for the extraction are water-immiscible solvents or the corresponding solvent mixtures, such as, for example, ethyl acetate, butyl acetate, toluene or methyl tert-butyl ether (MTBE). Concentration of the solution gives the product in good yield and high purity.

The crude product is purified either by washing the residue obtained, or by crystallization. Suitable for washing are, for example, water and aqueous solvents. Suitable for recrystallization are, for example, toluene and benzene.

In principle, in the context of further reaction for preparing active compounds, the crude product obtained can also be used for the next reaction step without further purification of the reaction solution. To this end, the reaction solution which contains the compounds of the formula I can be diluted with further solvents and thus be employed as crude solution for the next process step. Alternatively, it is also possible to concentrate the reaction solution and to transfer the resulting residue directly or as a melt into the next process step.

The compounds of the formula II to be used as starting materials are known from the literature and/or commercially available. They can be prepared by processes known per se, such as, for example, described in more detail in WO 98/31681 or WO 99/58509.

The invention is illustrated in more detail in the working examples below.

EXAMPLE 1

4-Bromo-2-(4,5-dihydroisoxazol-3-yl)-3-methylaniline

Brominating agent: $HBr/H_2O_2$ 100.5 g of 2-(4,5-dihydroisoxazol-3-yl)-3-methylaniline are initially charged in 2000 g of pyridine, and 98.2 g of HBr are added dropwise at 20–35° C. at 78–84° C., 64.6 g of hydrogen peroxide are then added dropwise over 0.5 h. The mixture is stirred at 25° C. for a further 12 hours and then concentrated until an oily residue remains. The crude product is, at 50° C., dissolved in 100 ml of pyridine and admixed with 1000 ml of water. The mixture is stirred at 0° C. for 1 h and then filtered off, and the filter residue is washed twice with 200 ml of water and dried.

This gives 141 g (yield: 92%) of a yellow solid (HPLC: 94.6% of 4-bromo-2-(4,5-dihydroisoxazol-3-yl)-3-methylaniline, 1.8% of 6-bromo-2-(4,5-dihydroisoxazol-3-yl)-3-methylaniline, 3.4% of 4,6-dibromo-2-(4,5-dihydroisoxazol-3-yl)-3-methylaniline).

EXAMPLE 2

4-Bromo-2-(4,5-dihydroisoxazol-3-yl)-3-methylaniline

Brominating agent: bromine 100 g of 2-(4,5-dihydroisoxazol-3-yl)-3-methylaniline are initially charged in 1000 g of pyridine, and a solution of altogether 96.19 g of bromine in 1000 g of pyridine is added dropwise at 20° C. in five freshly prepared portions, over 3 hours. The mixture is stirred for a further 12 hours. Pyridine is distilled off at 150 mbar and a bath temperature of 75° C. The residue is dissolved in 2 l of water and extracted repeatedly with in each case 250 ml of ethyl acetate. Concentration gives 122.1 g of product (yield 81.6%; GC: 93.2% of 4-bromo-2-(4,5-dihydroisoxazol-3-yl)-3-methylaniline, 2.7% of 6-bromo-2-(4,5-dihydroisoxazol-3-yl)-3-methylaniline, 4.1% of 4,6-dibromo-2-(4,5-dihydroisoxazol-3-yl)-3-methylaniline).

EXAMPLE 3

4-Bromo-2-(4,5-dihydroisoxazol-3-yl)-3-methylaniline

Brominating agent: bromine 5 g of the compound 2-(4,5-dihydroisoxazol-3-yl)-3-methylaniline are initially charged in 50 g of pyridine, and a solution of altogether 4.89 g of bromine in 50 g of pyridine (mixture to be prepared at 0° C.) is added dropwise at 20° C. over 5 h. The mixture is stirred at 25° C. for a further 12 hours. The batch is poured into 250 ml of water and extracted three times with in each case 100 ml of MTBE. The combined organic phases are washed twice with in each case 100 ml of water, dried over sodium sulfate and concentrated.

This gives 6.0 g of product (yield 79.8%; 94.3% of 4-bromo-2-(4,5-dihydroisoxazol-3-yl)-3-methylaniline, 1.8% of 6-bromo-2-(4,5-dihydroisoxazol-3-yl)-3-methylaniline, 3.5% of 4,6-dibromo-2-(4,5-dihydroisoxazol-3-yl)-3-methylaniline).

EXAMPLE 4

4-Bromo-2-(4,5-dihydroisoxazol-3-yl)-3-methylaniline

Brominating agent: HBr, $H_2O_2$ 500.0 g of 2-(4,5-dihydroisoxazol-3-yl)-3-methylaniline are initially charged in 4500 g of pyridine and 467.4 g of 47% HBr are added dropwise at 25–35° C. Under reflux and at atmospheric pressure, the water is distilled off azeotropically. At 100° C. 199.2 g of 50% hydrogen peroxide are added droperise over 2 hours. The mixture is stirred for 1 hour, cooled to room temperature and washed with a sodium sulfite solution, and then the solvent is removed (T<100° C.). The residue is taken up in 3220 g of dimethyl disulfide and washed with 1500 g water at 60° C. The resulting solution is used in the next reaction step.

This procedure yields about 83% of the desired product.

We claim:

1. A process for preparing 4-bromoaniline derivatives of the formula I

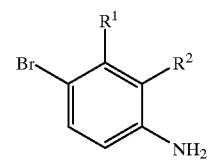

where:
$R^1$ is $C_1$–$C_6$-alkyl, $C_1$–$C_6$-haloalkyl, $C_1$–$C_6$-alkoxy, $C_1$–$C_6$-haloalkoxy, $C_3$–$C_8$-cycloalkyl, halogen $R^2$ is $C_1$–$C_6$-alkyl, $C_1$–$C_6$-alkoxy, $C_3$–$C_8$-cycloalkyl, $C_2$–$C_6$-alkenyl, cyano or a heterocyclic radical, which comprises reacting a compound of the formula II

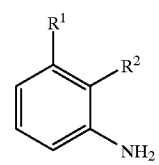

in which $R^1$ and $R^2$ are as defined above with a brominating agent in the solvent pyridine or a solvent mixture comprising at least 55% by weight of pyridine.

2. A process as claimed in claim 1, wherein the brominating agent used is bromine.

3. A process as claimed in claim 1, wherein the brominating agent used is hydrogen bromide and hydrogen peroxide.

4. A process as claimed in claim 1, where the solvent is pyridine.

5. A process as claimed in claim 1, where $R^1$ is $C_1$–$C_6$-alkyl.

6. A process as claimed in claim 5, wherein $R^1$ is methyl or ethyl.

7. A process as claimed in claim 1, where $R^2$ is a heterocyclic ring.

8. A process as claimed in claim 7, where $R^2$ is an isoxazole, isoxazoline or isoxazolidine ring.

9. A process as claimed in claim 8, where $R^2$ is 4,5-dihydroisoxazol-3-yl or 4,5-dihydroisoxazol-5-yl.

10. A process as claimed in claim 1 for preparing 4-bromo-2-(4,5-dihydroisoxazol-3-yl)-3-methylaniline.

11. A process as claimed in claim 1 for preparing 4-bromo-2-(4,5-dihydroisoxazol-3-yl)-3-methylaniline, where the brominating agent used is bromine.

12. A process as claimed in claim 1 for preparing 4-bromo-2-(4,5-dihydroisoxazol-3-yl)-3-methylaniline, where the brominating agent used is bromine and where the solvent is pyridine.

13. A process as claimed in claim 1 for preparing 4-bromo-2-(4,5-dihydroisoxazol-3-yl)-3-methylaniline, where the brominating agent used is bromine, where the solvent is pyridine and where the molar ratio of the brominating agent and the compound II is from 1:1 to 2:1.

14. A process as claimed in claim 1 for preparing 4-bromo-2-(4,5-dihydroisoxazol-3-yl)-3-methylaniline, where the brominating agent used is bromine, where the solvent is pyridine and where the brominating agent and the compound II are employed in equimolar amounts.

15. A process as claimed in claim 1 for preparing 4-bromo-2-(4,5-dihydroisoxazol-3-yl)-3-methylaniline, where the brominating agent used is bromine and where the solvent mixture comprises at least 55% by weight of pyridine.

16. A process as claimed in claim 1 for preparing 4-bromo-2-(4,5-dihydroisoxazol-3-yl)-3-methylaniline, where the brominating agent used is bromine, where the solvent mixture comprises at least 55% by weight of pyridine and where the molar ratio of the brominating agent and the compound II is from 1:1 to 2:1.

17. A process as claimed in claim 1 for preparing 4-bromo-2-(4.5-dihydroisoxazol-3-yl)-3-methylaniline, where the brominating agent used is bromine, where the solvent mixture comprises at least 55% by weight of pyridine and where the brominating agent and the compound II are employed in equimolar amounts.

18. A process as claimed in claim 1 for preparing 4-bromo-2-(4,5-dihydroisoxazol-3-yl)-3-methylaniline, where the brominating agent used is hydrogen bromide and hydrogen peroxide.

19. A process as claimed in claim 1 for preparing 4-bromo-2-(4,5-dihydroisoxazol-3-yl)-3-methylaniline, where the brominating agent used is hydrogen bromide and hydrogen peroxide and where the solvent is pyridine.

20. A process as claimed in claim 1 for preparing 4-bromo-2-(4,5-dihydroisoxazol-3-yl)-3-methylaniline, where the brominating agent used is hydrogen bromide and hydrogen peroxide, where the solvent is pyridine and where the molar ratio of the brominating agent and the compound II is from 1:1 to 2:1.

21. A process as claimed in claim 1 for preparing 4-bromo-2-(4,5-dihydroisoxazol-3-yl)-3-methylaniline, where the brominating agent used is hydrogen bromide and hydrogen peroxide. where the solvent is pyridine and where the brominating agent and the compound 11 are employed in equimolar amounts.

22. A process as claimed in claim 1 for preparing 4-bromo-2-(4,5-dihydroisoxazol-3-yl)-3-methylaniline, where the brominating agent used is hydrogen bromide and hydrogen peroxide and where the solvent mixture comprises at least 55% by weight of pyridine.

23. A process as claimed in claim 1 for preparing 4-bromo-2-(4,5-dihydroisoxazol-3-yl)-3-methylaniline, where the brominating agent used is hydrogen bromide and hydrogen peroxide, where the solvent mixture comprises at least 55% by weight of pyridine and where the molar ratio of the brominating agent and the compound II is from 1:1 to 2:1.

24. A process as claimed in claim 1 for preparing 4-bromo-2-(4,5-dihydroisoxazol-3-yl)-3-methylaniline, where the brominating agent used is hydrogen bromide and hydrogen peroxide, where the solvent mixture comprises at least 55% by weight of pyridine and where the brominating agent and the compound II are employed in equimolar amounts.

25. A process as claimed in claim 1 for preparing 4-bromo-2-(4,5-dihydroisoxazol-3-yl)-3-methylaniline, where the brominating agent used is pyridinium hydrobromide and hydrogen peroxide and where the solvent is pyridine.

26. A process as claimed in claim 1 for preparing 4-bromo-2-(4,5-dihydroisoxazol-3-yl)-3-methylaniline, where the brominating agent used is pyridinium hydrobromide and hydrogen peroxide, where the solvent is pyridine and where the molar ratio of the brominating agent and the compound II is from 1:1 to 2:1.

27. A process as claimed in claim 1 for preparing 4-bromo-2-(4,5-dihydroisoxazol-3-yl)-3-methylaniline, where the brominating agent used is pyridinium hydrobromide and hydrogen peroxide, where the solvent is pyridine and where the brominating agent and the compound II are employed in equimolar amounts.

28. A process as claimed in claim 1 for preparing 4-bromo-2-(4,5-dihydroisoxazol-3-yl)-3-methylaniline, where the brominating agent used is pyridinium hydrobromide and hydrogen peroxide and where the solvent mixture comprises at least 55% by weight of pyridine.

29. A process as claimed in claim 1 for preparing 4-bromo-2-(4,5-dihydroisoxazol-3-yl)-3-methylaniline, where the brominating agent used is pyridinium hydrobromide and hydrogen peroxide, where the solvent mixture comprises at least 55% by weight of pyridine and where the molar ratio of the brominating agent and the compound II is from 1:1 to 2:1.

30. A process as claimed in claim 1 for preparing 4-bromo-2-(4,5-dihydroisoxazol-3-yl)-3-methylaniline, where the brominating agent used is pyridinium hydrobromide and hydrogen peroxide, where the solvent mixture comprises at least 55% by weight of pyridine and where the brominating agent and the compound II are employed in equimolar amounts.

* * * * *

UNITED STATES PATENT AND TRADEMARK OFFICE
CERTIFICATE OF CORRECTION

PATENT NO. : 6,388,135 B1
DATED : May 14, 2002
INVENTOR(S) : Lochtman et al.

It is certified that error appears in the above-identified patent and that said Letters Patent is hereby corrected as shown below:

Column 9,
Line 56, "peroxide." should be -- peroxide, --;
Line 58, "11" should be -- II --.

Signed and Sealed this

Fifteenth Day of October, 2002

Attest:

JAMES E. ROGAN
Attesting Officer
Director of the United States Patent and Trademark Office